US011692164B2

(12) United States Patent
Pfannenstiel et al.

(10) Patent No.: US 11,692,164 B2
(45) Date of Patent: Jul. 4, 2023

(54) ANTIBIOTIC-FREE COMPOSITIONS FOR THE PREVENTION OR CONTROL OF COCCIDIOSIS

(71) Applicant: Huvepharma Inc., Peachtree City, GA (US)

(72) Inventors: Mary Ann Pfannenstiel, Lincoln, NE (US); Jennifer Albrecht, Waverly, NE (US); Glen M. Wilkinson, Brooks, GA (US)

(73) Assignee: Huvepharma Inc., Peachtree City, GA (US)

( * ) Notice: Subject to any disclaimer, the term of this patent is extended or adjusted under 35 U.S.C. 154(b) by 39 days.

(21) Appl. No.: 17/367,231

(22) Filed: Jul. 2, 2021

(65) Prior Publication Data

US 2021/0332322 A1 Oct. 28, 2021

Related U.S. Application Data

(62) Division of application No. 16/869,246, filed on May 7, 2020, now abandoned, which is a division of application No. 15/414,341, filed on Jan. 24, 2017, now abandoned.

(51) Int. Cl.
| | | |
|---|---|---|
| *C12N 1/10* | (2006.01) | |
| *C12N 1/04* | (2006.01) | |
| *A61K 39/012* | (2006.01) | |
| *A61K 39/00* | (2006.01) | |
| *A61K 35/68* | (2006.01) | |

(52) U.S. Cl.
CPC .............. *C12N 1/10* (2013.01); *A61K 39/012* (2013.01); *C12N 1/04* (2013.01); *A61K 35/68* (2013.01); *A61K 2039/51* (2013.01)

(58) Field of Classification Search
None
See application file for complete search history.

(56) References Cited

U.S. PATENT DOCUMENTS

| | | | |
|---|---|---|---|
| 3,147,186 A | 9/1964 | Edgar | |
| 3,435,141 A | 3/1969 | Hileman et al. | |
| 4,438,097 A | 3/1984 | Shirley | |
| 4,544,548 A | 10/1985 | Davis et al. | |
| 4,808,404 A | 2/1989 | Bhogal | |
| 5,055,292 A * | 10/1991 | McDonald | A61K 39/012 435/243 |
| 5,068,104 A | 11/1991 | Bhogal et al. | |
| 5,303,050 A | 4/1994 | Nishimura et al. | |
| 5,311,841 A | 5/1994 | Thaxton | |
| 5,405,862 A | 4/1995 | Farina et al. | |
| 5,495,146 A | 2/1996 | Saito et al. | |
| 5,523,852 A | 6/1996 | Sowerby et al. | |
| 5,990,967 A | 11/1999 | Kawakami et al. | |
| 6,495,146 B1 | 12/2002 | Evans et al. | |
| 6,500,438 B2 | 12/2002 | Evans et al. | |
| 6,627,205 B2 | 9/2003 | Evans et al. | |
| 6,908,620 B2 | 6/2005 | McDougald et al. | |
| 6,998,127 B2 | 2/2006 | McDougald et al. | |
| 7,018,640 B2 | 3/2006 | Evans et al. | |
| 7,229,615 B2 * | 6/2007 | Conkle | C12N 1/10 435/243 |
| 7,354,593 B2 | 4/2008 | McDougald et al. | |
| 7,436,456 B2 | 10/2008 | Morel et al. | |
| 7,846,685 B2 * | 12/2010 | Schasteen | C12N 1/10 435/69.3 |
| 9,050,281 B2 | 6/2015 | Lang et al. | |
| 10,781,418 B2 | 9/2020 | Pfannenstiel et al. | |
| 2002/0093590 A1 | 7/2002 | Hodgkiss et al. | |
| 2003/0171307 A1 * | 9/2003 | Boettner | A61K 9/0019 514/28 |
| 2006/0104996 A1 | 5/2006 | Hutchins et al. | |
| 2010/0015182 A1 * | 1/2010 | Lang | A61P 33/00 424/269.1 |
| 2018/0208885 A1 | 7/2018 | Pfannenstiel et al. | |
| 2019/0382712 A1 | 12/2019 | Pfannenstiel et al. | |
| 2020/0015182 A1 | 1/2020 | Yuan et al. | |
| 2020/0370003 A1 | 11/2020 | Pfannenstiel et al. | |

FOREIGN PATENT DOCUMENTS

| | | |
|---|---|---|
| CN | 105287447 A | 2/2016 |
| DE | 40 30 148 A1 | 3/1992 |
| EP | 0 256 878 A2 | 2/1988 |
| EP | 0 516 378 A1 | 12/1992 |
| GB | 2398956 B | 5/2006 |
| JP | S6399019 A | 4/1988 |
| JP | 2001119607 A | 4/2001 |
| JP | 20090037141 A | 2/2009 |

(Continued)

OTHER PUBLICATIONS

Begum (Prevalence of Formalin Contamination and its Effect on Organoleptic Characteristics of Giant Fresh Water Prawn in Different Markets of Mymensingh, 2013). (Year: 2013).*

Ayaz, M.M. et al., "Immunoglobulin producing cells in chickens immunized with Eimeria tenella gametocyte antigen vaccines," Veterinarni Medicina, vol. 53 (4): 207-213 (2008).

Barbour, T. et al., "Thrombotic microangiopathy and associated renal disorders," Nephrology Dialysis Transplantation, vol. 27(7):2673-2685 (2012).

Chapin, J.C. et al., "Use of Anti-O5 Monoclonal Antibody Eculizumab in the Treatment of a Patient with Refractory Idiopathic Thrombotic Thrombocytopenic Purpura (TTP)—Abstract 4666," Blood, vol. 118 (21): 5 pages (2011) Retrieved from the Internet: URL:http://www.bloodjournal.org/content/118/21/4666?sso-checked=true>.

(Continued)

*Primary Examiner* — Nghi V Nguyen
(74) *Attorney, Agent, or Firm* — Nelson Mullins Riley & Scarborough LLP

(57) ABSTRACT

Compositions are provided that contain sporulated coccidial oocysts, wherein the compositions are free of antibiotics and comprise formalin at a concentration sufficient to inhibit microbial growth for at least 12 months while maintaining oocyst viability. Methods of preparing such compositions are also provided.

7 Claims, No Drawings

(56) References Cited

FOREIGN PATENT DOCUMENTS

| | | |
|---|---|---|
| JP | 2011521955 A | 7/2011 |
| WO | 94/16725 A1 | 8/1994 |
| WO | 96/40233 A1 | 12/1996 |
| WO | 2009148895 A1 | 12/2009 |

OTHER PUBLICATIONS

Cowan, M. et al., "Plant Products as Antimicrobial Agents," Clinical Microbiology Reviews, vol. 12 (4): 564-582 (1999).

Dubey, J.P. et al., "The Toxoplasma Gondii Oocyst from Cat feces," J Exp Med., vol. 132 (4):636-662 (1970).

Environmental Health & Safety, "List of Disinfectants, Fact Sheet, Properties of Commonly-Used Laboratory Disinfectants For Surface Cleaning," Princeton University, 2 pages, retrieved on Feb. 18, 2019.

European Search Report, European Application No. 18744498.9, dated Aug. 12, 2020, 6 pages.

Chroustova, E. et al., The Efficiency of Disinfectants on the Oocysts of Eimeria,: Acta Vet. Brno., vol. 56: 141-149(1987).

United States Environmental Protection Agency, Office of Chemical Safety and Pollution Prevention, List A: EPA's Registered Antimicrobial Products as Sterilizers, Aug. 15, 2016, 4 pages.

International Search Report and Written Opinion for corresponding PCT Application No. PCT/US18/15102, dated Apr. 23, 2018.

J. Bacteriol Parasitol vol. 5 Issue 4 2014.

Office Action and Search Report, Taiwan Patent Application No. 107102580, dated Dec. 6, 2018, 8 pages.

Rao, S. et al., "Sterilization and Disinfection," www.microrao.com , 10 pages (2008).

Sharman, P.A., et al., "Chasing the Golden Egg: Vaccination against Poultry Coccidiosis," Parasite Immunology, vol. 32: 590-598 (2010).

Supplementary European Search Report completed Aug. 4, 2020 for counterpart foreign application No. EP 18744498, 6 pages.

Tewari, K.K., et al. "Control of Poultry Coccidiosis: Changing Trends," J. Parasit Dis (JPD), vol. 35: 10-17 (2011).

* cited by examiner

ANTIBIOTIC-FREE COMPOSITIONS FOR THE PREVENTION OR CONTROL OF COCCIDIOSIS

CROSS-REFERENCE TO RELATED APPLICATIONS

The present application is a division of U.S. patent application Ser. No. 16/869,246, filed May 7, 2020, which is a division of U.S. patent application Ser. No. 15/414,341, filed Jan. 24, 2017 (ABANDONED), the entire disclosure of each of which are hereby incorporated by reference as if set forth verbatim herein and relied upon for all purposes.

BACKGROUND OF THE INVENTION

Coccidiosis is a disease of various animals in which the intestinal mucosa is invaded and damaged by a protozoa of the subclass Coccidia. The economic effects of coccidiosis can be especially severe in the poultry industry where intensive housing of birds favors the spread of the disease. Infection by coccidial protozoa is, for the most part, species specific. Numerous species, however, can infect a single host. For example, there are seven species of coccidial protozoa that infect chickens, six of which are considered to be moderately to severely pathogenic.

The life cycle of the coccidial parasite is complex. For example, protozoa of the genera *Eimeria, Isospora*, Cystoisospora, or *Cryptosporidium* typically only require a single host to complete their life cycle, although Cystoisospora may utilize an intermediate host. Under natural conditions, the life cycle begins with the ingestion of sporulated oocysts from the environment. When sporulated oocysts are ingested by a susceptible animal, the wall of the sporulated oocyst is broken in order to release the sporocysts inside. In poultry, the release of the sporocyst is the result of mechanical disruption of the sporulated oocyst in the gizzard. Within the sporocysts, are the sporozoites which are the infective stage of the organism. In poultry, the breakdown of the sporocyst coat and release of the sporozoites is accomplished biochemically through the action of chymotrypsin and bile salts in the small intestine. Once released, the sporozoites invade the intestinal mucosa or epithelial cells in other locations. The site of infection is characteristic of the species involved. For example, in the genus *Eimeria, E. tenella* is localized in the ceca; *E. necatrix* is found in the anterior and middle portions of the small intestine; *E. acervulina* and *E. praecox* occur in the upper half of the small intestine; *E. brunetti* occurs in the lower small intestine, rectum, ceca, and cloaca; *E. mitis* is found in the lower small intestine, while *E. maxima* can be found in any of these physiological locations.

Once inside the host animals' cells, sporozoites develop into multinucleate meronts, also called schizonts. Each nucleus of the meront develops into an infective body called a merozoite which enters new cells and repeats the process. After a variable number of asexual generations, merozoites develop into either microgametocytes or macrogametes. Microgametocytes develop into many microgametes which, in turn, fertilize the macrogametes. A resistant coat then forms around the resulting zygotes. The encysted zygotes are called oocysts and are shed unsporulated in the feces. Infected birds may shed oocysts in the feces for days or weeks. Under proper conditions of temperature and moisture, the oocysts become infective through the process of sporulation. Susceptible birds then ingest the sporulated oocysts through normal pecking activities or ground/litter foraging and the cycle repeats itself. Ingestion of viable, sporulated oocysts is the only natural means of infection.

Infection with coccidial protozoa results in immunity so that the incidence of the disease decreases over time as members of the flock become immune. This self-limiting nature of coccidial infections is widely known in chickens and other poultry. The immunity conferred, however, is species specific such that introduction of another species of coccidial protozoa will result in a new disease outbreak.

The oocyst wall of coccidial protozoa provides a highly effective barrier for oocyst survival. Oocysts may survive for many weeks outside the host. In the laboratory, intact oocysts are resistant to extremes in pH, detergents, proteolytic, glycolytic, and lipolytic enzymes, mechanical disruption, and chemicals such as sodium hypochlorite and dichromate.

Two methods are currently used to control coccidiosis in poultry. The first involves control by chemotherapy. Numerous drugs are available for the control of coccidiosis in poultry. Because of the number of species that cause the disease, very few drugs are efficacious against all species, although a single drug may be efficacious against several species. In modern broiler chicken production, for example, administration of drugs to control coccidiosis is routine. The expense for preventative medication against coccidiosis represents a significant cost of production.

Furthermore, the development of drug resistance by Coccidia is a serious limitation on the effectiveness of chemotherapy to control the disease. Surveys in the United States, South America and Europe have revealed widespread drug resistance in Coccidia. Since drug resistance is a genetic phenomenon, once established, drug resistance can remain in the population for many years until reduced by natural selection pressure and genetic drift.

The use of drugs in animals used for food production is also coming under increasing scrutiny by the public. Consumers are increasingly concerned with the possibility of drug residues in food. This creates pressure in the poultry industry to reduce the use of drugs to control coccidiosis.

Vaccination of birds against coccidiosis is an alternative to chemotherapy. An advantage of vaccination is that it can greatly reduce or eliminate the need to administer anti-coccidial drugs, thus reducing drug costs to poultry producers, preventing the development of drug-resistant strains, and lessening consumer concerns about drug residues.

Numerous methods have been developed to immunize poultry against coccidial protozoa. Most methods have been based on the administration of live protozoa, either fully virulent strains or attenuated strains. The most common route of administration is oral, although other routes have been used. Edgar, U.S. Pat. No. 3,147,186, teaches vaccination of chickens by oral administration either directly into the mouth or via the feed or water of viable *E. tenella* sporulated oocysts. Davis et al., U.S. Pat. No. 4,544,548, teaches a method of vaccination by continuous administration of low numbers of sporulated oocysts, with or without simultaneous administration of anti-coccidial drugs.

Oral administration of attenuated strains of sporocysts has also been utilized to confer immunity against coccidiosis. Shirley, U.S. Pat. No. 4,438,097; McDonald, U.S. Pat. No. 5,055,292; and Schmatz et al., PCT publication No. WO 94/16725. An alternative to attenuation is disclosed in Jenkins et al., Avian Dis., 37(1):74-82 (1993), which teaches the oral administration of sporozoites that have been treated with gamma radiation to prevent merogonic development.

Furthermore, parenteral routes of vaccination have been used, including subcutaneous or intraperitoneal injection of excysted sporozoites (Bhogal, U.S. Pat. No. 4,808,404; Bhogal et al., U.S. Pat. No. 5,068,104) and intra ovo injection of either oocysts or sporocysts (Evans et al., PCT publication No. WO 96/40233; Watkins et al., Poul. Sci., 74(10):1597-602 (1995)). Sharma, J. Parasitol., 50(4):509-517 (1964), reported unsuccessful immunization trials involving intravenous, intraperitoneal, intramuscular, or subcutaneous injection of either viable oocysts or a mixture of oocysts, sporocysts and sporozoites. Thaxton, U.S. Pat. No. 5,311,841, teaches a method of vaccination against Coccidia by administration of oocysts or sporozoites to newly hatched chicks by yolk sac injection.

Production of Coccidiosis vaccines that use live *Eimeria* oocysts involves a step to sanitize the oocysts. For example, sodium hypochlorite has been used to achieve sanitization, but due to the tremendous microbial bioburden in the feces from which *Eimeria* is isolated, there may be some residual bioburden. In the United States the residual bioburden in oral vaccines for chickens may not exceed one colony forming unit (CFU) per dose. In order to hold the microbial bioburden in check within the vaccine preparation, antibiotics have been used in Coccidiosis vaccines. However, there is concern regarding the use of antibiotics in farm animals. Moreover, there is a growing strong consumer demand for farm animals that have not been treated with any antibiotics.

Thus, it would be highly advantageous to eliminate the need to add antibiotics to coccidial vaccine preparations while still holding the microbial bioburden in check within the preparations over long term storage.

SUMMARY OF THE INVENTION

Coccidiosis is a disease of animals that has a significant economic impact, especially in the poultry industry. In many poultry operations, birds are vaccinated against coccidiosis using vaccines containing sporulated oocysts. Present methods for the storage of sporulated coccidial oocysts use added antibiotics to control microbial bioburden. The present invention provides compositions and methods for the storage of sporulated coccidial oocysts, including coccidial vaccine preparations, wherein the microbial bioburden is inhibited without the use of antibiotics. In the compositions and methods of the invention, an optimal concentration of formalin is added to compositions of viable sporulated coccidial oocysts such that the microbial growth is inhibited for at least 12 months while not significantly affecting the viability of the sporulated oocysts.

Accordingly, in one aspect, the invention pertains to a composition for the prevention or control of coccidiosis comprising viable sporulated oocysts of at least one species of protozoa known to cause coccidiosis, wherein said composition is free of antibiotics and comprises formalin at a concentration of 0.006%-0.008% such that microbial growth in the composition is inhibited for at least 12 months. In one embodiment, the composition comprises formalin at a concentration of about 0.007%. In another embodiment of the method, the final concentration of formalin is 0.007%. In one embodiment, the composition is also free of potassium dichromate. In one embodiment, the oocysts are present in the composition at a concentration of at least 1000 oocysts/ml, or 5000 oocysts/ml or 10,000 oocysts/ml.

In one embodiment, the viable sporulated oocysts are *Eimeria* oocysts. For example, in one embodiment, the composition comprises viable sporulated oocysts of *Eimeria acervulina*, *Eimeria maxima* and *Eimeria tenella*. Other suitable oocysts from other species of protozoa known to cause coccidiosis are described herein. In one embodiment, the sporulated oocysts are wild type oocysts. In another embodiment, the sporulated oocysts are attenuated oocysts.

In one embodiment, the composition further comprises a diluent, such as water. In one embodiment, the aqueous diluent comprises 0.5× phosphate buffered saline. In other embodiments, the diluent comprise a buffer such as a phosphate buffer, a bicarbonate buffer, a citric acid buffer or a tris buffer. In one embodiment, the buffer controls pH between about 6.8 and about 7.8.

In another aspect, the invention pertains to a method of preparing a composition for the prevention or control of coccidiosis, the method comprising:

preparing a composition of viable sporulated oocysts of at least one species of protozoa known to cause coccidiosis, wherein the composition further comprises a diluent and is free of antibiotics; and adding formalin to the composition to a final concentration of 0.006%-0.008%;

wherein microbial growth in the composition is inhibited for at least 12 months.

In one embodiment of the method, the final concentration of formalin is about 0.007%. In another embodiment of the method, the final concentration of formalin is 0.007%. In one embodiment, the composition is also free of potassium dichromate. In one embodiment, the oocysts are present in the composition at a concentration of at least 1000 oocysts/ml, or 5000 oocysts/ml or 10,000 oocysts/ml.

In one embodiment, the viable sporulated oocysts are *Eimeria* oocysts. For example, in one embodiment, the method comprises preparing a composition comprising viable sporulated oocysts of *Eimeria acervulina*, *Eimeria maxima* and *Eimeria tenella*. Other suitable oocysts from other species of protozoa known to cause coccidiosis are described herein. In one embodiment, the sporulated oocysts are wild type oocysts. In another embodiment, the sporulated oocysts are attenuated oocysts.

In one embodiment of the method, the diluent is water. In one embodiment, the aqueous diluent comprises 0.5× phosphate buffered saline. In other embodiments, the diluent comprise a buffer such as a phosphate buffer, a bicarbonate buffer, a citric acid buffer or a tris buffer. In one embodiment, the buffer controls pH between about 6.8 and about 7.8.

In addition to the compositions and methods above relating to coccidial vaccine preparations for control or prevention of coccidiosis, the invention also provides compositions and methods for long term storage of viable sporulated oocysts, which can then be used in the preparation of vaccine compositions.

Accordingly, in another aspect, the invention pertains to a composition for storage of sporulated coccidial oocysts, the composition comprising viable sporulated oocysts of at least one species of protozoa known to cause coccidiosis, wherein the composition is free of antibiotics and comprises formalin at a concentration of 0.01%-0.025% such that microbial growth in the composition is inhibited for at least 12 months. In one embodiment, the composition is also free of potassium dichromate. In one embodiment, the oocysts are present in the composition at a concentration of at least 1000 oocysts/ml, or 5000 oocysts/ml or 10,000 oocysts/ml.

In one embodiment, the composition comprises viable sporulated oocysts from an *Eimeria* species. For example, in one embodiment, the composition comprises viable sporulated oocysts of *Eimeria acervulina*. In another embodiment, the composition comprises viable sporulated oocysts of *Eimeria maxima*. In yet another embodiment, the composition comprises viable sporulated oocysts of *Eimeria tenella*. Other suitable oocysts from other species of protozoa known to cause coccidiosis are described herein. In one embodiment, the sporulated oocysts are wild type oocysts. In another embodiment, the sporulated oocysts are attenuated oocysts.

In one embodiment, the composition comprises formalin at a concentration of 0.01%. In another embodiment, the composition comprises formalin at a concentration of 0.025%.

In yet another aspect, the invention pertains to methods of preparing a composition for storage of sporulated coccidial oocysts, the method comprising:

preparing a suspension of viable sporulated oocysts of at least one species of protozoa known to cause coccidiosis, wherein the suspension is free of antibiotics; and adding formalin to the suspension to a final concentration of 0.01%-0.025%, such that microbial growth in the composition is inhibited for at least 12 months.

In one embodiment, the suspension is also free of potassium dichromate. In one embodiment, the oocysts are present in the suspension at a concentration of at least 1000 oocysts/ml, or 5000 oocysts/ml or 10,000 oocysts/ml.

In one embodiment of the method, the suspension comprises viable sporulated oocysts from an *Eimeria* species. For example, in one embodiment, the suspension comprises viable sporulated oocysts of *Eimeria acervulina*. In another embodiment, the suspension comprises viable sporulated oocysts of *Eimeria maxima*. In yet another embodiment, the suspension comprises viable sporulated oocysts of *Eimeria tenella*. Other suitable oocysts from other species of protozoa known to cause coccidiosis are described herein. In one embodiment, the sporulated oocysts are wild type oocysts. In another embodiment, the sporulated oocysts are attenuated oocysts.

In one embodiment of the method, the final concentration of formalin in the suspension is 0.01%. In another embodiment of the method, the final concentration of formalin in the suspension is 0.025%.

DETAILED DESCRIPTION OF THE INVENTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications, databases and other references cited in this application are herein incorporated by reference in their entirety as if each individual publication, patent, patent application, database or other reference were specifically and individually indicated to be incorporated by reference.

As used herein, the terms "formaldehyde" and "formalin" are used interchangeable to refer to the aldehyde with the chemical formula $H_2CO$. Typically formaldehyde is used in the art to refer to the compound in gaseous form, whereas formalin is typically used in the art to refer to a solution of formaldehyde in water.

As used herein, the term "about", with respect to a percent concentration (e.g., "about 0.025%" or "about 0.007%", is intended to encompass slight variations from the stated numerical value, e.g., no more than a 25% variation either higher or lower than the stated numerical value.

The present invention provides for the elimination of added antibiotics in compositions of sporulated coccidial oocysts, including coccidiosis vaccines, having a long shelf life (e.g., at least 12 months). In the compositions and methods of the invention, an optimal concentration of formalin is used to inhibit microbial growth, rather than antibiotics, thereby providing antibiotic-free formulations of coccidiosis vaccines. In the compositions and methods of the invention, sporulated coccidial oocysts that have been sanitized such that their starting bioburden is low are used in the preparation of stock preparations and vaccine preparations wherein an optimal concentration of formalin is added to the oocysts (rather than using antibiotics) to thereby inhibit microbial growth for an extended period of time without significantly inhibiting the viability of the sporulated oocysts.

As demonstrated in the Examples, formalin was demonstrated to be more effective than a panel of other compounds tested in its ability to inhibit microbial growth without significantly impacting oocysts viability. Additionally, as demonstrated in the Examples, a concentration range of about 0.01-0.025% formalin was found to be optimally effective in inhibiting microbial growth in stock preparations of sporulated *Eimeria* oocysts stored for at least 12 months, without significantly impacting oocyst viability. Still further, as demonstrated in the Examples, a concentration range of about 0.006-0.008%, such as about 0.007%, preferably a concentration of 0.007%, of formalin was found to be optimally effective in inhibiting microbial growth in vaccine preparations of sporulated *Eimeria* oocysts stored for at least 12 months, without significantly impacting oocyst viability.

Accordingly, in one aspect, the invention pertains to compositions for long-term storage of sporulated coccidial oocysts, such as stock preparations that can be used in the formulation of coccidial vaccines. Such stock preparations typically contain a single strain of coccidial oocysts and can be used for the formulation of vaccines. Accordingly, in another aspect, the invention pertains to coccidial vaccine preparations. Such vaccine preparations typically contain multiple strains of sporulated coccidial oocysts, and may contain additional constituents, such as diluents, buffers, and the like. In yet another aspect, the invention pertains to methods of preparing sporulated coccidial oocyst compositions (e.g., stock preparations) and vaccine preparations.

Oocyst Stock Preparations

The invention provides compositions and methods for long term storage of viable sporulated coccidial oocysts, which can be used, for example, in the preparation of vaccine compositions. Such compositions are referred to herein as stock preparations, and are also referred to in the art as bulk lots or antigen lots. The stock preparations of the invention allow for long term-storage (e.g., at least 12 months) with a low microbial bioburden (e.g., 1-10 CFUs/ml or less) without the use of antibiotics.

In one embodiment, the invention provides a composition for storage of sporulated coccidial oocysts, the composition comprising viable sporulated oocysts of at least one species of protozoa known to cause coccidiosis, wherein the composition is free of antibiotics and comprises formalin at a concentration of 0.01%-0.025% such that microbial growth in the composition is inhibited for at least 12 months. In one embodiment, the composition is also free of potassium dichromate. The viable sporulated oocysts are sanitized (e.g., as described further below) such that they have a low starting bioburden when added to the composition (e.g., 1-10 CFUs/ml or less).

Typically, the stock preparation compositions of the invention contain a single coccidial strain, although in alternative embodiments multiple strains can be included in the stock preparation compositions. In one embodiment, the oocysts are of at least one species of protozoa known to cause coccidiosis in poultry. In another embodiment, the oocysts are of at least one species of protozoa known to cause coccidiosis in chickens. In another embodiment, the oocysts are of at least one species of protozoa known to cause coccidiosis in turkeys.

In one embodiment, the composition comprises viable sporulated oocysts from an *Eimeria* species that causes coccidiosis in chickens. In one embodiment, the composition contains sporulated oocysts of a single *Eimeria* species. In another embodiment, the composition contains sporulated oocysts of more than one *Eimeria* species (e.g., two, three, four, five or more species). In one embodiment, the composition comprises viable sporulated oocysts of *Eimeria acervulina*. In another embodiment, the composition comprises viable wild type sporulated oocysts of *Eimeria maxima*. In yet another embodiment, the composition comprises viable sporulated oocysts of *Eimeria tenella*. In another embodiment, the composition comprises viable sporulated oocysts of *Eimeria necatrix*. In another embodiment, the composition comprises viable sporulated oocysts of *Eimeria mivati*. In another embodiment, the composition comprises viable sporulated oocysts of *Eimeria mitis*. In another embodiment, the composition comprises viable sporulated oocysts of *Eimeria praecox*. In another embodiment, the composition comprises viable sporulated oocysts of *Eimeria brunetti*. In one embodiment, the compositions comprise viable wild type sporulated oocysts of any of the aforementioned *Eimeria* strains. In yet other embodiments, the composition comprises viable attenuated sporulated oocysts of any of the aforementioned *Eimeria* strains.

In another embodiment, the composition comprises viable sporulated oocysts from an *Eimeria* species that causes coccidiosis in turkeys. In one embodiment, the composition contains sporulated oocysts of a single *Eimeria* species. In another embodiment, the composition contains sporulated oocysts of more than one *Eimeria* species (e.g., two, three, four, five or more species). In one embodiment, the composition comprises viable sporulated oocysts of *Eimeria meleagrimitis*. In another embodiment, the composition comprises viable sporulated oocysts of *Eimeria adenoeides*. In yet another embodiment, the composition comprises viable sporulated oocysts of *Eimeria gallopavonis*. In another embodiment, the composition comprises viable sporulated oocysts of *Eimeria dispersa*. In another embodiment, the composition comprises viable sporulated oocysts of *Eimeria meleagridis*. In another embodiment, the composition comprises viable sporulated oocysts of *Eimeria innocua*. In another embodiment, the composition comprises viable sporulated oocysts of *Eimeria subrotunda*. In one embodiment, the compositions comprise viable wild type sporulated oocysts of any of the aforementioned *Eimeria* strains. In yet other embodiments, the composition comprises viable attenuated sporulated oocysts of any of the aforementioned *Eimeria* strains.

In another embodiment, the sporulated oocysts are of the coccidial genus *Isospora*. In another embodiment, the sporulated oocysts are of the coccidial genus Cystoisospora. In another embodiment, the sporulated oocysts are of the coccidial genus *Cryptosporidium*. In one embodiment, the composition comprises viable wild type sporulated oocysts of any of the aforementioned strains. In other embodiments, the composition comprises viable attenuated sporulated oocysts of any of the aforementioned strains.

In one embodiment, the composition comprises formalin at a concentration of about 0.01%. In one embodiment, the composition comprises formalin at a concentration of 0.01%. In one embodiment, the composition comprises formalin at a concentration of about 0.015%. In one embodiment, the composition comprises formalin at a concentration of 0.015%. In one embodiment, the composition comprises formalin at a concentration of about 0.020%. In one embodiment, the composition comprises formalin at a concentration of 0.020%. In one embodiment, the composition comprises formalin at a concentration of about 0.025%. In another embodiment, the composition comprises formalin at a concentration of 0.025%.

In various embodiments, the viable sporulated oocysts are present in the composition at a concentration of at least 50 oocysts/ml or 100 oocysts/ml or 200 oocysts/ml or 500 oocysts/ml or 1000 oocysts/ml or 5000 oocysts/ml or 10,000 oocysts/ml.

In another aspect, the invention provides methods of preparing a composition for storage of sporulated coccidial oocysts, the method comprising:

preparing a suspension of viable sporulated oocysts of at least one species of protozoa known to cause coccidiosis, wherein the suspension is free of antibiotics; and adding formalin to the suspension to a final concentration of 0.01%-0.025%, such that microbial growth in the composition is inhibited for at least 12 months.

Suitable oocyst species for use in the method are those set forth above with respect to the compositions.

Suitable final concentrations of formalin include those set forth above with respect to the compositions.

In one embodiment, the suspension is also free of potassium dichromate.

The viable sporulated oocysts used in the suspension are sanitized (e.g., as described further below) such that they have a low starting bioburden when used in the above method (e.g., 1-10 CFUs/ml or less).

While the final concentration of formalin in the suspension is 0.01%-0.025%, the ordinarily skilled artisan will readily appreciate that a higher concentration of formalin can be used in the method and then diluted down such that a final concentration of 0.01%-0.025% formalin is achieved for the long-term storage composition.

Vaccine Preparations

The stock preparations of the invention can be used in the preparation of vaccines for prevention or control of coccidiosis, e.g., in poultry. Accordingly, in another embodiment, the invention provides a composition for the prevention or control of coccidiosis comprising viable sporulated oocysts of at least one species of protozoa known to cause coccidiosis, wherein said composition is free of antibiotics and comprises formalin at a concentration of 0.006%-0.008% such that microbial growth in the composition is inhibited for at least 12 months. In one embodiment, the composition comprises formalin at a concentration of about 0.007%. In yet another embodiment, the composition comprises formalin at a concentration of 0.007%. In one embodiment, the composition is also free of potassium dichromate. The viable sporulated oocysts are sanitized (e.g., as described further below) such that they have a low starting bioburden when added to the composition (e.g., 1-10 CFUs/ml or less).

Typically, the vaccine compositions of the invention contain multiple coccidial strains (e.g., two, three, four, five or more strains). In one embodiment, the oocysts are of at least one species of protozoa known to cause coccidiosis in poultry. In another embodiment, the oocysts are of at least one species of protozoa known to cause coccidiosis in chickens. In another embodiment, the oocysts are of at least one species of protozoa known to cause coccidiosis in turkeys.

In one embodiment, the composition comprises viable sporulated oocysts from an *Eimeria* species that causes coccidiosis in chickens. In one embodiment, the composition comprises viable sporulated oocysts from three or more *Eimeria* species that causes coccidiosis in chickens. In one embodiment, the composition comprises viable sporulated oocysts of *Eimeria acervulina, Eimeria maxima* and *Eimeria tenella*. In another embodiment, the composition comprises viable sporulated oocysts of multiple (e.g., two, three, four, five or more) *Eimeria* strains selected from the group consisting of *Eimeria acervulina, Eimeria maxima, Eimeria tenella, Eimeria necatrix, Eimeria mivati, Eimeria mitis, Eimeria praecox* and *Eimeria* brunetti. In one embodiment, the composition comprises viable wild type sporulated oocysts of any of the aforementioned *Eimeria* strains (e.g., oocysts of two, three, four, five or more wild type forms of the aforementioned *Eimeria* strains). In yet other embodiments, the composition comprises viable attenuated sporulated oocysts of any of the aforementioned *Eimeria* strains (e.g., oocysts of two, three, four, five or more attenuated forms of the aforementioned *Eimeria* strains).

In another embodiment, the composition comprises viable sporulated oocysts from an *Eimeria* species that causes coccidiosis in turkeys. In one embodiment, the composition comprises viable sporulated oocysts from three or more *Eimeria* species that causes coccidiosis in turkeys. In another embodiment, the composition comprises viable sporulated oocysts of multiple (e.g., two, three, four, five or more) *Eimeria* strains selected form the group consisting of *Eimeria* meleagrimitis, *Eimeria* adenoeides, *Eimeria* gallopavonis, *Eimeria dispersa, Eimeria meleagridis, Eimeria innocua* and *Eimeria* subrotunda. In one embodiment, the composition comprises viable wild type sporulated oocysts of any of the aforementioned *Eimeria* strains (e.g., oocysts of two, three, four, five or more wild type forms of the aforementioned *Eimeria* strains). In yet other embodiments, the composition comprises viable attenuated sporulated oocysts of any of the aforementioned *Eimeria* strains (e.g., oocysts of two, three, four, five or more attenuated forms of the aforementioned *Eimeria* strains).

In another embodiment, the sporulated oocysts are of the coccidial genus *Isospora*. In another embodiment, the sporulated oocysts are of the coccidial genus Cystoisospora. In another embodiment, the sporulated oocysts are of the coccidial genus *Cryptosporidium*. In one embodiment, the composition comprises viable wild type sporulated oocysts of any of the aforementioned strains. In other embodiments, the composition comprises viable attenuated sporulated oocysts of any of the aforementioned strains.

In one embodiment, the composition further comprises a diluent, such as water. In one embodiment, the aqueous diluent comprises 0.5× phosphate buffered saline. In other embodiments, the diluent comprise a buffer such as a phosphate buffer, a bicarbonate buffer, a citric acid buffer or a tris buffer. In one embodiment, the buffer controls pH between about 6.8 and about 7.8.

In a further embodiment, a concentrated vaccine may be diluted prior to administration, for example, from 10 milliliters to about a 250 milliliter. In another embodiment, the concentrated vaccine may be diluted prior to administration from about 10 milliliters to about 2.5 Liters.

In various embodiments, the viable sporulated oocysts are present in the vaccine at a concentration of at least 50 oocysts/ml or 100 oocysts/ml or 200 oocysts/ml or 500 oocysts/ml or 1000 oocysts/ml or 5000 oocysts/ml or 10,000 oocysts/ml. In yet other embodiments, the viable sporulated oocysts are present in the vaccine at a concentration of 50-200 oocysts/dose or 50-500 oocysts/dose or at least 50 oocysts/dose or at least 100 oocysts per dose or at least 200 oocysts/dose.

The vaccine compositions can be administered to animals, through various routes, including, but not limited to orally, e.g., by addition to food or water; topically, e.g., spraying; parenteral routes, e.g. subcutaneous, intramuscular or intraperitoneal injection; per os or via intra-yolk sac injection. Vaccine compositions also can be administered in ovo (i.e., into a bird egg containing a live, developing embryo), e.g., as described in U.S. Pat. Nos. 6,495,146; 6,500,438; 6,627, 205; and 7,018,640.

In another aspect, the present invention provides for a kit comprising a composition for the prevention or control of coccidiosis comprising viable sporulated oocysts of at least one species of protozoa known to cause coccidiosis, wherein said composition is free of antibiotics and comprises formalin at a concentration of 0.006%-0.008% such that microbial growth in the composition is inhibited for at least 12 months; and instructions for administration of said composition to an animal. In one embodiment, the composition comprises formalin at a concentration of about 0.007%. In yet another embodiment, the composition comprises formalin at a concentration of 0.007%.

In yet another aspect, the invention provides a method of preparing a composition for the prevention or control of coccidiosis, the method comprising:

preparing a composition of viable sporulated oocysts of at least one species of protozoa known to cause coccidiosis, wherein the composition is free of antibiotics; and adding formalin to the composition to a final concentration of 0.006%-0.008%;

wherein microbial growth in the composition is inhibited for at least 12 months.

In one embodiment of the method, the final concentration of formalin is about 0.007%. In another embodiment of the method, the final concentration of formalin is 0.007%.

In one embodiment, the composition is also free of potassium dichromate.

The viable sporulated oocysts used in the method are sanitized (e.g., as described further below) such that they have a low starting bioburden when added to the composition (e.g, 1-10 CFUs/ml or less).

In one embodiment, the composition is made from one or more stock preparations of coccidial oocysts containing formalin at a concentration of 0.01%-0.025%, wherein the stock preparation(s) is diluted such that the final concentration of the formalin in the composition is reduced to 0.006%-0.008% (e.g., about 0.007% or 0.007%).

Suitable oocyst species for use in the method are those set forth above with respect to the compositions.

Suitable diluents and buffers for use in the method include those set forth above with respect to the compositions.

Production of Sanitized Sporulated Coccidial Oocysts

The compositions and methods of the invention use sanitized sporulated coccidial oocysts to create antibiotic free preparations for control or prevention of coccidiosis. Methods for isolating, sporulating and sanitizing coccidial oocysts are well established in the art (e.g., as described in U.S. Pat. No. 7,846,685). Regardless of the route of administration, procedures for the production of coccidiosis vaccines are quite similar. Briefly, coccidial protozoa are produced by infecting host animals with a single species of coccidial protozoa. These "seed stocks" are often clonal in nature, that is, derived from a single organism in order to insure the presence of only the species of interest. Seed stocks may be wild type, that is, isolated from the field, or they may be precocious or attenuated strains. The protozoa are then allowed to undergo replication in the host, after which, protozoa are collected from the animals, usually from the excreta. The use of attenuated strains typically results in fewer shed oocysts from the host animal. The protozoa are then separated from the excreta by well known techniques such as salt floatation and centrifugation.

Oocysts used in the practice of the present invention can be obtained from a variety of sources. For example, oocysts can be obtained by the inoculation of host animals with coccidial protozoa of a single species. The coccidial protozoa used can be clonal in nature, that is, derived from a single progenitor, or polyclonal. The oocysts of the present composition are derived from wild type oocysts. Inoculation can be by any means that will allow for the replication of the protozoa in the host animal. The most common route of inoculation is per os, but other suitable routes may be used. If administered per os, the protozoa are preferably at the sporulated oocyst stage. Administration can be by gavage or through the feed and/or water. Inoculation can also be accomplished by exposing host animals to environments contaminated with coccidial protozoa. Alternatively, oocysts can be obtained from animals with naturally occurring infections.

After oral inoculation of host animals (e.g., with an *Eimeria* species), manure from the inoculated animals is then collected from the inoculated host animals. Oocysts are separated from the manure using a combination of isolation techniques, including sieving, centrifugation and density flotation. The isolated oocysts are then sporulated under certain defined conditions controlling factors such as temperature, percent saturation of dissolved oxygen, pH, and agitation in a sporulation medium. The sporulated oocysts are then separated from the sporulation medium and sanitized. After, the sporulated oocysts have been separated from the sporulation medium and sanitized they are combined with a diluent or a diluent and a buffer to form a vaccine. A post-challenge performance improvement composition may also then be added. Such a composition ameliorates a decrease in post-challenge performance. The amelioration may be seen in factors such as bursal growth and appearance.

Once host animals begin shedding the organism, the protozoa can be collected. Most commonly, protozoa are collected from the feces, but they can also be collected from intestinal contents and/or scrapings as well as contaminated bedding. Once collected, the oocysts are preferably isolated from the extraneous fecal material as decreasing the fecal content in an oocyst suspension increases the number of oocysts that will sporulate (Smith and Ruff, Poultry Sci. 54:2083, 1975). A preferred method for isolating oocysts is by sieving. However, several methods for isolating protozoa are known in the art and may be used in practicing the present invention. A review of several methods for the isolation of oocysts can be found in Ryley et al. (Parasitology 73:311-326, 1976).

Another method for separating oocysts from droppings comprises flotation using solutions of sufficient specific gravity, typically having a specific gravity of about 1.2, so that oocysts float to the top of the suspension. Generally these solutions are made up of water to which a sugar (e.g. sucrose), $ZnSO_4$, or NaCl has been added to increase the specific gravity to the desired value. Useful solutions include solutions comprising 58% (w/v) sucrose, 37% (w/v) $ZnSO_4X7H_2O$ and saturated NaCl solutions, which all have a specific gravity from about 1.09 to about 1.2. Other solutions which have a comparable specific gravity and are not harmful to the oocysts can also be used.

In the flotation method of isolation, a preliminary step of filtering diluted collected manure through, e.g., gauze, a sieve or cheesecloth to remove large particles of undesired fecal matter may be included. After mixing harvested oocysts with the flotation solution, the oocyst slurry may be centrifuged and the oocyst removed from the surface layer of the supernatant or in the supernatant. The centrifugation step may be repeated several times to further purify the oocysts by resuspending the captured supernatant in a flotation medium having a specific gravity similar to that used in previous centrifugation steps and centrifuged again. This step may be repeated until the desired level of purity is reached.

Another method for isolation of oocysts available in the art comprises gradient centrifugation. The gradient used can be discontinuous or continuous. An example of a typical gradient for coccidial oocysts is 0-50% sucrose. In this method the material containing the oocysts is placed on top of the gradient and the oocyst containing material is then centrifuged along with the gradient. Following centrifugation, the layer containing the oocysts is recovered. The process may be repeated in order to increase the purity of the resulting oocyst preparation. As with flotation, this method is preferably preceded by filtration of the collected manure.

Additional methods of oocyst isolation include, the use of glass bead columns (Ryley et al., Parasitology, 73:311-326, 1976) and the bicarbonate ether method (Smith and Ruff, Poultry Sci. 54:2081-2086, 1975). In the glass column method, the aqueous suspension of fecal matter is added to a mixture of glass beads and a detergent, for example 5% Tween 80. The mixture is then applied to a column of glass beads and the oocysts are allowed to flow through while much of the undesired fecal matter is retained in the column. The effluent may then be concentrated by centrifugation.

In the bicarbonate ether method, the feces from infected chickens is strained, through cheese cloth for example, and the liquid fraction is captured while the solid fraction is discarded. The liquid fraction is then concentrated by centrifugation. The solid fraction is recovered and the supernatant is discarded. The recovered solid fraction is then resuspended in a solution of 1% sodium bicarbonate. To the resuspended solid fraction, now in suspension, is then added ether in a volume approximately equal to the volume of 1% solution of sodium bicarbonate. The mixture is then centrifuged. The debris plug and supernatant is discarded while the sediment is washed by resuspension in water. This suspension is then centrifuged and the supernatant discarded. The sediment is then recovered for use. (Smith and Ruff, Poultry Sci. 54:2081-2086, 1975).

Another method of purifying and concentrating oocysts involves subjecting the aqueous fraction obtained from the initial purification steps to solid/liquid phase centrifugal-based separation by means of a hydrocyclone, as described in U.S. Pat. No. 7,846,685.

The various methods for isolating, concentrating, and purifying oocysts described above may be used in combination with one another or in combination with the preferred embodiments of the instant invention. Regardless of the methods used, the greater the isolation, concentration, and purification the greater percent sporulation during the sporulation suite.

At the time of collection, the protozoa are at the non-infective oocyst stage of the life cycle. In order to become infective, and therefore useful for vaccines, the oocysts must be induced to undergo sporulation. Methods of sporulating coccidial oocysts are well established in the art. Any suitable method known in the art for sporulating coccidial oocysts can be used to obtain sporulated oocysts for use in the compositions and methods of the invention.

Sporulation may be performed in any suitable container, however, a fermentation vessel is preferred in order to best control temperature, dissolved oxygen, pH, and mixing in addition to monitoring these parameters of the sporulation medium. The capacity of the sporulation vessel varies with batch size and can be adequately selected by one skilled in the art. A preferred fermentor is the New Brunswick Bio-Flow (available from New Brunswick Scientific Company, Edison, N.J.).

Sporulation is achieved by subjecting the oocysts to an oxidative challenge. In this step, the oocysts are contacted with an oxidizing agent which is effective to promote sporulation but does not result in the death of the oocysts. Typically, the oxidizing agent comprises a principal oxidant other than a source of dichromate. Preferably, the sporulation medium is substantially devoid of potassium dichromate, an alkali metal dichromate, dichromate ions or other dichromate salt.

Sporulation can be achieved by depositing concentrated oocysts in a fermentation vessel, subjecting the oocysts to an oxidative challenge by contacting the oocysts with an oxidizing agent, such as oxygen or sodium hypochlorite, in an aqueous medium, wherein the percent saturation of dissolved oxygen in the medium is maintained at preferred levels, pH is controlled between preferred levels by the alternative addition of an acid or a base, the suspension is mixed to near homogeneity, and temperature is between preferred temperatures over a preferred period of time. An anti-foaming agent can be added during the sporulation process.

One suitable oxidizing agent used for sporulation is oxygen. Oxygen may be added in the form of air or as pure oxygen. Another suitable oxidizing agent used for sporulation is sodium hypochlorite.

During sporulation, the percent saturation of dissolved oxygen content in the aqueous medium is maintained typically at least 30%-50% of saturation. Percent saturation of dissolve oxygen is controlled, by supplying air or molecular oxygen, to achieve consistent and higher yields of sporulated oocysts.

Percent saturation of dissolved oxygen can be maintained by bubbling air through the mixture at a rate sufficient to meet the above ranges. Pure oxygen may also be bubbled through the mixture to maintain the requisite percent dissolved oxygen. Care should be taken so that the flow of oxygen is not so rapid as to cause foaming. If desired, an anti-foaming agent may be added, such as Antifoam A (available from Sigma-Aldrich, St. Louis, Mo.). Oxygen is added by any means practicable. Oxygen may be added by adding both air when lesser flow rates are needed. e.g., when oxygen consumption is relatively low to peak sporulation, to maintain the preferred percent dissolved oxygen saturation while molecular oxygen may be added when the need is greater, e.g., when oxygen consumption is greatest. Oxygen is preferably added at a flow rate of from about 0.1 to about 2.0 liters of gas per liter of material and more preferably from about 0.3 to about 0.5 liters of gas per liter of material. The flow rate may be kept constant despite a greater need to maintain preferred percent saturation of dissolved oxygen as the gas added may consist of air when less oxygen is needed and may consist of molecular oxygen when more oxygen is needed. The preferred fermentor automatically converts from the addition of air to molecular oxygen as needed while controlling a nearly constant flow rate.

The pH level is preferably maintained from about 7.0 to about 7.7, more preferably from 7.2 to about 7.5, and more preferably still the pH is maintained about 7.4. The pH level of the sporulation medium is controlled by adding an acid or a base. In a preferred embodiment, either sodium hydroxide (5N) or sulfuric acid (5N) is alternatively added to the sporulation medium as needed to maintain the pH near 7.4. When using a fermentation vessel, the acid and/or the base may be added by using a fermentation vessel's automatically controlled peristaltic pumps on the fermentor.

The temperature of the sporulation medium is controlled throughout sporulation. Oocysts are placed in a sporulation vessel at a temperature that substantially avoids freezing to about 43° C.; preferably between about 15° C. to about 38° C.; and more preferably between about 20° C. to 30° C. and more preferably still at about 28° C.±1° C. It will be apparent to those of ordinary skill in the art that the rate of sporulation is temperature dependent, so that the time required for sporulation will generally be less at higher temperatures.

Throughout the sporulation process, the sporulation medium is mixed. Any suitable method of mixing can be used to mix the sporulation medium to about a homogenous state. The exact method of mixing varies depending on the container used. For example, when bottles or flasks are used, mixing can be achieved by the use of shakers, or magnetic or mechanical stirrers. When vats or fermentors are used, a mechanical stirrer, such as a paddle stirrer is preferred.

Although sporulation is substantially complete within 12 to 18 hours, removal of the sporulated oocysts prior to about 72 hours decreases viability. Therefore, sporulated oocysts are preferably kept under the above sporulation conditions for a preferred time period to provide a more stable population of sporulated oocysts. The oocysts are preferably maintained in the above conditions for approximately 72 to 120 hours, more preferably for 72 to 110 hours, and more preferably still for 72 to 96 hours, to allow sporulation to occur.

Monitoring of sporulation will assist the practitioner in reaching higher yields of viable sporulated oocysts. Optionally, sporulation can be confirmed by microscopic examination of the oocysts.

Following sporulation, the sporulated oocysts, are removed from the sporulation vessel, and washed free of the sporulation medium and concentrated by any suitable method, preferably filtration. The entire sanitization process is generally conducted in two phases: (1) contaminants may be first removed non-aseptically; followed by (2) sanitization of sporulated oocysts medium carried out under aseptic conditions. The purpose of this process is to collect sporulated oocysts and filter out contaminants. A further purpose is to concentrate oocysts, preferably by filtration. However, centrifugation may also be used to concentrate the sporulated oocysts. A further purpose is to sanitize the suspension with a disinfectant, preferably sodium hypochlorite (leaving the sporulated oocysts intact), then to remove the disinfectant from and then concentrate the sporulated oocysts.

In one embodiment, separation of the sporulated oocysts from the sporulation medium may be achieved by centrifugal-based separation, such as by bottle centrifuge, decanter centrifuge, or by hydrocyclone. The volume of the batch size will be determinative of the mode of centrifugal-based separation and can be determined by one skilled in the art. The solid fraction from any one of the centrifugal-based separation methods is recovered. If more than about 5% of the oocysts loaded into the centrifugal-based separation unit are in the refuse fraction, a liquid fraction in this embodiment, said refuse fraction is mixed with the solid fraction and recycled through the centrifugal-based separation unit. The recovered solids are then diluted to a volume appropriate for sanitization, preferably by filtration, more preferably by tangential flow filtration.

Sporulated oocysts can be concentrated by methods known in the art, such as by filtration (e.g., as described in U.S. Pat. No. 7,846,685). Once the sporulated oocysts have been concentrated, they can be sanitized by means of a chemical disinfectant or disinfecting agent other than an alkali metal dichromate, soluble dichromate moieties, dichromate ions, or potassium dichromate. Sanitization processes are conducted in sterile environments. In a preferred embodiment, sanitization is accomplished within the filtration device used to concentrate the sporulated oocysts. In an alternative embodiment the retentate containing the sporulated oocysts can be washed from the filter and sanitization is accomplished in a vessel separate from the filtration device. Any filtration unit used to sanitize the sporulated oocysts should be sterilized prior to the addition of the unsterilized sporulated oocysts. In one embodiment, the filtration unit is sterilized by autoclaving. In an alternative embodiment, the filtration unit is sterilized by passing steam at approximately 250° C. through the system for at least about 30 minutes at approximately 20 psi. In yet another alternative embodiment, the unit is chemically sterilized by treating the system with 5% sodium hypochlorite for at least about 10 minutes wherein the sodium hypochlorite contains at least about 5% available chlorine by weight.

The agent used for sanitizing the sporulated oocysts preferably is one that kills bacteria and viruses, but does not kill the sporulated oocysts. Preferably, the disinfectant used kills the infectious bursal disease (IBDV), chick anemia (CAV) viruses, and related bacteria.

In a preferred embodiment, the disinfectant used is sodium hypochlorite. The concentration of disinfectant used varies with the agent chosen to accomplish sanitization. In more preferred embodiment, sodium hypochlorite is used at a concentration preferably in the range from about 1% to about 10%, and more preferably in the range of about 2% to about 5% wherein the percent represents the percent of available chlorine by weight. The time during which the sporulated oocysts are exposed to the disinfectant varies depending upon factors such as the concentration of the disinfectant and the volume of the batch of sporulated oocysts. In one embodiment, the sporulated oocysts are treated with approximately 5% sodium hypochlorite, wherein the percent represents the percent of available chlorine by weight, from about 2 to about 20 minutes, more preferably from about 5 to about 18 minutes, and most preferably for about 10 minutes.

For the purposes of the present invention, sporulated oocysts and compositions containing sporulated oocysts are considered sanitized if samples of liquids containing the oocysts do not have detectable amounts of live bacteria or fungi, IBD virus or CAV virus. Detection of live bacteria or fungi, IBD virus or CAV virus can be accomplished by any method known in the art (e.g., as described in U.S. Pat. No. 7,846,685).

Sanitized sporulated oocysts are preferably stored at any temperature between room temperature and a low temperature that substantially avoids freezing. In a preferred embodiment, the sporulated oocysts are stored at between about 1° C. and about 10° C., more preferably between about 2° C. to about 7° C., and in a most preferred embodiment between about 4° C. to about 5° C. In an alternative embodiment, the sporulated oocysts are stored at a temperature between 20° C. to about 30° C., more preferably between 22° C. to about 27° C., and most preferably at about 25° C.

Although not necessary, a buffering agent may be added to the diluent in which the sporulated oocysts are stored. Buffers are utilized in the storage composition as they prolong viability over the use of sterile water. Many suitable buffers are known in the art including, but not limited to, phosphate buffer, bicarbonate buffer, citric acid and tris buffers. In one preferred embodiment, the diluent comprises 0.5×PBS. In a preferred embodiment, a volume of buffer is used that results in a concentration of sporulated oocysts suitable for transfer to containers that are ultimately used by the consumer as a vaccine for the prevention of coccidiosis.

In yet another embodiment, the diluent used for storage purposes includes a composition that ameliorates a decrease in post-challenge performance and thickening agents to maintain the sporulated oocysts in suspension. Suitable thickening agents include starches, gums, polysaccharides, and mixtures thereof. Suitable compositions to ameliorate a decrease in post-challenge performance include, but are not limited to, cytokines, growth factors, chemokines, mitogens and adjuvants. Such compositions to improve post-challenge performance are well known to those skilled in the art and can be found, for example, in Plotkin and Orenstein, Vaccines, Third Ed., W.B. Saunders, 1999; Roitt et al., Immunology, Fifth Ed., Mosby, 1998; and Brostoff, et al., Clinical Immunology, Gower Medical Publishing, 1991. Examples of compositions to improve post-challenge performance, include, but are not limited to, Alum (aluminum phosphate or aluminum hydroxide), Freund's adjuvant, calcium phosphate, beryllium hydroxide, dimethyl dioctadecyl ammonium bromide, saponins, polyanions, e.g. poly A:U, Quil A, inulin, lipopolysaccharide endotoxins, liposomes, lysolecithins, zymosan, propionibacteria, mycobacteria, and cytokines, such as, interleukin-1, interleukin-2, interleukin-4, interleukin-6, interleukin-12, interferon-.alpha., interferon-.gamma., granulocyte-colony stimulating factor. In one preferred embodiment, the diluent includes *Propionibacterium acnes* (*P. acnes*) at from between 10 μg and 100 μg per dose (dry weight) and more preferred at about 50 μg per dose (dry weight). The preferred concentration is from about 3.0 to about 5.0 milligrams per milliliter of vaccine, most preferably about 4.2 milligrams per milliliter.

In a further embodiment of the present invention, sanitized sporulated oocysts are stored in a composition comprising an oxidizing agent. The oxidizing agent preferably has a reduction potential of greater than 0.5 V, more preferably between 0.75 and 3.0 V, most preferably between about 1.0 and 2.0 V in the sporulation medium. The oxygen present in sterile water may also be used as the oxidizing agent. When sterile water, or any other oxidizing agent is used, no additional oxygen or air is incorporated in to the storage composition. Examples of other suitable oxidizing agents include, but are not limited to, aqueous bromine, chlorine dioxide, hydrogen peroxide, potassium permanganate, potassium perchlorate, sodium hypochlorite, and hydrochlorous acid which have reduction potentials of about 1.09 V, 1.64 V, 1.78 V, 1.49 V, 1.37 V, 1.49 V, and 1.63 V, respectively. The requisite amount of oxidizing agent added varies with the agent used and the species of protozoa and can be determined empirically by one skilled in the art. For protozoa of the genus *Eimeria*, preferred concentrations of the oxidizing agents once added to the sporulated oocyst suspension include from about 0.1 to about 0.75 wt % for potassium perchlorate, from about 0.5 to about 2.9 wt % for potassium permanganate, from about 0.001 to about 0.1 wt % sodium hypochlorite and from about 1 ppm to about 5 ppm for hydrochlorous acid.

EXAMPLES

The following examples are intended to provide illustrations of the application of the present invention. The following examples are not intended to completely define or otherwise limit the scope of the invention.

Example 1: Inhibition of Microbial Bioburden in Eimeria Oocyst Samples by Addition of Formalin at Various Concentrations The model chosen to examine the effect of different concentrations of formalin on the level of microbial bioburden in *Eimeria* oocyst samples utilized *Bacillus subtilis* and *Penicillium chrysogenum*. Cultures of each of these organisms were prepared and diluted to stocks containing either 10-100 or 1-10 cfu/mL. A low level of organisms (0-10 cfu/mL) is more typical of the amount of bioburden detected following sanitization of oocysts, so this is the target for the preservative. The preservative was added at the desired concentration after sanitization of lots of *Eimeria* oocysts An aliquot of *Eimeria acervulina* oocysts was removed following sanitization and prior to addition of gentamicin and Amphotericin B. The oocysts were spiked with *B. subtilis* and *P. chrysogenum* at a concentration of either 1-10 cfu/mL or 10-100 cfu/mL. Formalin was added to a final concentration of either 0.01% or 0.025%, according to the treatment group descriptions in Table 1 below. Vials of each treatment group were then stored at 2-7° C., and observed monthly up to 1 year for visible growth of the organisms. The results observed with respect to visible microbial growth are summarized in Table 1.

TABLE 1

Inhibition of microbial growth by formalin in *E. acervulina* oocysts after 12 months of storage

| Treatment Group | Oocysts Added | *B. subtilis/ P. chrysogenum* Added (cfu/mL) | Final Formalin Concentration (%) | Observations (Incubation at 2-7° C.) |
|---|---|---|---|---|
| 1 | Yes | 0 | 0 | NG |
| 2 | No | 10-100 | 0 | G |
| 3 | Yes | 10-100 | 0 | G |
| 4 | No | 1-10 | 0 | G |
| 5 | Yes | 1-10 | 0 | G |
| 6 | Yes | 0 | 0.025 | NG |
| 7 | Yes | 10-100 | 0.025 | NG |
| 8 | Yes | 1-10 | 0.025 | NG |
| 9 | Yes | 0 | 0.010 | NG |
| 10 | Yes | 10-100 | 0.010 | G |
| 11 | Yes | 1-10 | 0.010 | NG |

G = Growth; NG = No Growth.

The results demonstrated that when formalin was added to oocysts at a concentration of 0.025%, visible growth of *B. subtilis* and *P. chrysogenum*, at both 1-10 and 10-100 cfu/mL, was inhibited when stored for up to 12 months at refrigerated temperatures. Formalin added at a concentration of 0.010% inhibited visible growth of ~1-10 cfu/mL *B. subtilis* and *P. chrysogenum*, but not 10-100 cfu/mL.

Thus, overall, these studies demonstrated that 0.025% formalin was found to be the most effective concentration for inhibiting microbial bioburden at either 1-10 or 10-100 cfu/mL, while the lower concentration of 0.01% formalin was similarly effective for inhibiting microbial bioburden at 1-10 cfu/mL.

Example 2: Inhibition of Microbial Bioburden in a Coccidiosis Vaccine Preparation by Addition of Formalin In this example, an antibiotic-free version of the ADVENT® coccidiosis vaccine, containing *E. acervulina, E. maxima* and *E. tenella* oocysts but lacking gentamicin and amphotericin B (referred to herein as AF ADVENT) was prepared and then was spiked with *B. subtilis* and *P. chrysogenum* at either 1-10 or 10-100 CFU/ml. Formalin was then added to a final concentration of either 0.0028% or 0.0071%, according to the treatment group description in Table 2 below. Vials of each treatment group were then stored at 2-7° C., and observed monthly up to 1 year for visible growth of the organisms. The results observed with respect to visible microbial growth are summarized in Table 2.

TABLE 2

Inhibition of microbial growth by formalin in AF ADVENT after 12 months of storage

| Treatment Group | Vaccine Added | *B. subtilis/ P. chrysogenum* Added (cfu/mL) | Final Formalin Concentration (%) | Observations (Incubation at 2-7° C.) |
|---|---|---|---|---|
| 1 | Yes | 0 | 0 | NG |
| 2 | No | 10-100 | 0 | G |
| 3 | Yes | 10-100 | 0 | G |
| 4 | No | 1-10 | 0 | G |
| 5 | Yes | 1-10 | 0 | G |
| 6 | Yes | 0 | 0.0071 | NG |
| 7 | Yes | 10-100 | 0.0071 | G |
| 8 | Yes | 1-10 | 0.0071 | NG |
| 9 | Yes | 0 | 0.0028 | NG |
| 10 | Yes | 10-100 | 0.0028 | G |
| 11 | Yes | 1-10 | 0.0028 | G |

G = Growth; NG = No Growth.

All treatment groups were observed for the presence of macroscopic growth after twelve months of incubation. Visible growth was observed when *B. subtilis* and *P. chrysogenum* were added to the vaccine containing 0.0028% formalin. At a final formalin concentration of 0.0071% however, visible growth was only observed when the bioburden was ~10-100 cfu/mL *B. subtilis* and *P. chrysogenum*, but was not observed at a bioburden of ~1-10 cfu/mL. Since a bioburden of 1-10 cfu/mL is typical of the amount of bioburden detected following sanitization of oocysts, these results demonstrate that a final formalin concentration of 0.0071% in the final vaccine preparation is effective for inhibition of microbial bioburden.

Example 3: Effect of Formalin on Oocyst Viability

The effect of formalin on oocyst viability was investigated using oocyst lots of each *Eimeria* species (*E. acervulina, E. maxima* and *E. tenella*) and on vaccine. Viability was determined initially prior to the addition of formalin, and then after 1 year of storage at 2-7° C. The results are summarized in Table 3 below.

TABLE 3

Viability of *Eimeria* Oocysts lots and Vaccine after Storage for 12 Months

% Viable Oocysts after Storage for 12 Months

| Formalin Concentration | *E. acervulina* Initial | 12 mo | *E. maxima* Initial | 12 mo | *E. tenella* Initial | 12 mo | Vaccine Serial Initial | 12 mo |
|---|---|---|---|---|---|---|---|---|
| 0.000 | 85 | 48 | 69 | 32 | 93 | 92 | Not Applicable | |
| 0.010 | | 59 | | 47 | | 95 | | |
| 0.025 | | 27 | | 41 | | 86 | | |
| 0.0000 | Not Applicable | | | | | | 90 | 81 |
| 0.0028 | | | | | | | | 83 |
| 0.0071 | | | | | | | | 84 |

The results demonstrated that following 1 year in storage, formalin at 0.010% or lower concentrations did not have an adverse effect on oocyst viability. Formalin added at 0.025% affected the viability of only *E. acervulina* oocysts following long term storage.

A separate study demonstrated that use of higher concentrations of formalin resulted in increased toxicity towards the oocysts as compared to use of 0.025% or lower, thereby indicating the preferability of concentrations of 0.025% or lower for maintaining oocyst viability. Exemplary results from these studies are shown below in Table 4:

TABLE 4

Effect of Higher Concentrations of Formalin on Oocyst Viability

| *Eimeria* species | Time Stored at 2-7° C. | % Formalin | Decrease in Viability* |
|---|---|---|---|
| maxima | 2 weeks | 0.675% | 49% |
| acervulina | 4 months | 0.1% | 37% |

*Compared to same lot of oocysts stored with 0% Formalin

In the vaccine preparations, the presence of a final concentration of either 0.0028% or 0.0071% formalin did not affect oocyst viability.

Example 4: Effect of Additional Disinfectants on Oocyst Viability

In this example, additional disinfectant compounds were tested for their ability to inhibit microbial growth in *Eimeria* oocyst samples as compared to formalin. *E. maxima* oocysts were spiked with *B. subtilis* and *P. chrysogenum*, and the minimal inhibitory concentrations of several disinfectants were determined. The disinfectants were then added to *E. maxima* oocysts and the oocysts were stored at 2-7° C. for 6 months. The oocysts were assayed for viability and the decrease in viability due to the disinfectant was calculated by comparison to the same lot of oocysts stored in 0.5×PBS only. Exemplary results are summarized below in Table 5.

TABLE 5

Effect of disinfectants at minimal inhibitory concentration on oocyst viability following 6 months of storage at 2-7 C.

| Disinfectant | Minimal Inhibitory Concentration | Decrease in Viability* |
|---|---|---|
| Citral | 0.0125% | 24% |
| Thymol | 0.0063% | 15% |

*Compared to same lot of oocysts stored with 0% disinfectant

The results demonstrated that the other disinfectant compounds tested affected oocyst viability to a significantly greater extent than formalin, thereby demonstrating the advantageous properties of formalin in inhibiting microbial bioburden while not significantly impacting oocyst viability.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A composition for the prevention or control of coccidiosis comprising viable sporulated oocysts of at least one species of protozoa known to cause coccidiosis, wherein said composition is free of antibiotics and comprises formalin at a concentration of 0.0071%, wherein microbial bioburden in the composition is 1-10 CFUs/mL or less of *Bacillus subtilis* or *Penicillium chrysogenum* for at least 12 months, wherein the composition comprises viable sporulated oocysts of *Eimeria acervulina*, *Eimeria maxima*, and *Eimeria tenella*.

2. The composition of claim 1, which further comprises a diluent.

3. The composition of claim 2, wherein the diluent comprises water.

4. The composition of claim 3, wherein the aqueous diluent comprises 0.5X phosphate buffered saline.

5. The composition of claim 3, which further comprises a buffer.

6. The composition of claim 5, wherein the buffer is selected from the group consisting of phosphate buffers, bicarbonate buffers, citric acid buffers and tris buffers.

7. The composition of claim 6, wherein the buffer controls pH between about 6.8 and about 7.8.